(12) United States Patent
Gozani et al.

(10) Patent No.: US 10,384,063 B2
(45) Date of Patent: Aug. 20, 2019

(54) APPARATUS AND METHOD FOR AUTOMATED COMPENSATION OF TRANSCUTANEOUS ELECTRICAL NERVE STIMULATION FOR TEMPORAL FLUCTUATIONS SUCH AS CIRCADIAN RHYTHMS

(71) Applicant: Neurometrix, Inc., Waltham, MA (US)

(72) Inventors: Shai N. Gozani, Brookline, MA (US); Xuan Kong, Acton, MA (US)

(73) Assignee: Neurometrix, Inc., Waltham, MA (US)

( * ) Notice: Subject to any disclaimer, the term of this patent is extended or adjusted under 35 U.S.C. 154(b) by 0 days.

(21) Appl. No.: 15/648,173

(22) Filed: Jul. 12, 2017

(65) Prior Publication Data

US 2018/0015285 A1 Jan. 18, 2018
US 2019/0001130 A9 Jan. 3, 2019

Related U.S. Application Data

(63) Continuation-in-part of application No. 14/253,628, filed on Apr. 15, 2014.

(60) Provisional application No. 62/361,698, filed on Jul. 13, 2016.

(51) Int. Cl.
*A61N 1/36* (2006.01)
*A61N 1/04* (2006.01)
*A61N 1/372* (2006.01)

(52) U.S. Cl.
CPC ....... *A61N 1/36021* (2013.01); *A61N 1/0456* (2013.01); *A61N 1/36128* (2013.01); *A61N 2001/37294* (2013.01)

(58) Field of Classification Search
None
See application file for complete search history.

(56) References Cited

U.S. PATENT DOCUMENTS

| | | | |
|---|---|---|---|
| 1,741,962 | A | 12/1929 | Theodoropulos |
| D263,869 | S | 4/1982 | Sumiyasu |
| 4,503,863 | A | 3/1985 | Katims |
| 4,605,010 | A | 8/1986 | McEwen |
| 4,738,250 | A | 4/1988 | Fulkerson et al. |
| 4,989,605 | A | 2/1991 | Rossen |

(Continued)

FOREIGN PATENT DOCUMENTS

| | | |
|---|---|---|
| CN | 1919139 | 2/2007 |
| CN | 101626804 | 1/2010 |

(Continued)

OTHER PUBLICATIONS

Ancoli-Israel, S. et al., The Role of Actigraphy in the Study of Sleep and Circadian Rhythms, Sleep, 2003, 26(3), p. 342-392.

(Continued)

*Primary Examiner* — Brian T Gedeon
(74) *Attorney, Agent, or Firm* — Pandiscio & Pandiscio

(57) ABSTRACT

Apparatus for transcutaneous electrical nerve stimulation in a user, the apparatus comprising: stimulation means for electrically stimulating at least one nerve with at least one stimulation pulse; control means connected to the stimulation means for controlling at least one characteristic of the at least one stimulation pulse; and modulating means connected to the control means for modulating the at least one characteristic of the at least one stimulation pulse according to the time of day.

19 Claims, 9 Drawing Sheets

(56) References Cited

U.S. PATENT DOCUMENTS

| | | |
|---|---|---|
| 5,048,523 A | 9/1991 | Yamasawa et al. |
| 5,063,929 A | 11/1991 | Bartelt et al. |
| 5,121,747 A | 6/1992 | Andrews |
| 5,169,384 A | 12/1992 | Bosniak et al. |
| D342,571 S | 12/1993 | Givens, Sr. |
| D346,029 S | 4/1994 | Shalvi |
| 5,350,414 A | 9/1994 | Kolen |
| 5,429,589 A | 7/1995 | Cartmell et al. |
| 5,479,939 A | 1/1996 | Ogino |
| 5,487,759 A | 1/1996 | Bastyr et al. |
| 5,562,718 A | 10/1996 | Palermo |
| 5,806,522 A | 9/1998 | Katims |
| D411,887 S | 7/1999 | Agarwala |
| 5,948,000 A | 9/1999 | Larsen et al. |
| 6,099,488 A | 8/2000 | Hung |
| 6,161,044 A | 12/2000 | Silverstone |
| 6,266,558 B1 | 7/2001 | Gozani et al. |
| D450,313 S | 11/2001 | Koinuma |
| 6,430,450 B1 | 8/2002 | Bach-y-Rita et al. |
| D462,772 S | 9/2002 | Lamping et al. |
| 6,456,884 B1 | 9/2002 | Kenney |
| 6,662,051 B1 | 12/2003 | Eraker et al. |
| D541,042 S | 4/2007 | Andre et al. |
| D566,383 S | 4/2008 | Harris et al. |
| D592,200 S | 5/2009 | Liu |
| D598,556 S | 8/2009 | Chen |
| D600,352 S | 9/2009 | Cryan |
| D607,198 S | 1/2010 | Andre et al. |
| D609,353 S | 2/2010 | Cryan |
| 7,668,598 B2 | 2/2010 | Herregraven et al. |
| D611,611 S | 3/2010 | Sachi et al. |
| D615,526 S | 5/2010 | Andre et al. |
| 7,720,548 B2 | 5/2010 | King |
| 7,725,193 B1 | 5/2010 | Chu |
| 7,787,946 B2 | 8/2010 | Stahmann et al. |
| D625,829 S | 10/2010 | Arbesman et al. |
| D629,115 S | 12/2010 | Robertson |
| D636,881 S | 4/2011 | Clemens et al. |
| D637,988 S | 5/2011 | Jinkinson |
| 8,108,049 B2 | 1/2012 | King |
| 8,121,702 B2 | 2/2012 | King |
| 8,131,374 B2 | 3/2012 | Moore et al. |
| D658,302 S | 4/2012 | Nixon |
| D680,735 S | 4/2013 | Itabashi et al. |
| 8,421,642 B1 | 4/2013 | McIntosh et al. |
| D688,707 S | 8/2013 | Vincent et al. |
| D705,428 S | 5/2014 | Cheney et al. |
| D712,045 S | 8/2014 | Thornton |
| 8,825,175 B2 | 9/2014 | King |
| 8,862,238 B2 | 10/2014 | Rahimi et al. |
| D716,963 S | 11/2014 | Yosef et al. |
| 8,948,876 B2 * | 2/2015 | Gozani ............... A61N 1/0456 607/46 |
| D732,682 S | 6/2015 | Porat |
| 9,168,375 B2 | 10/2015 | Rahimi et al. |
| D744,661 S | 12/2015 | Rizzi |
| D750,263 S | 2/2016 | Shigeno et al. |
| D750,798 S | 3/2016 | Yosef et al. |
| D754,355 S | 4/2016 | Ganapathy et al. |
| D754,973 S | 5/2016 | Danze et al. |
| D757,292 S | 5/2016 | Chen |
| D758,605 S | 6/2016 | Chen |
| D758,606 S | 6/2016 | Chen |
| D759,262 S | 6/2016 | Chen |
| D759,263 S | 6/2016 | Chen |
| D759,958 S | 6/2016 | Requa |
| D762,628 S | 8/2016 | Yoon et al. |
| D762,872 S | 8/2016 | Chen |
| D767,775 S | 9/2016 | Gilmer et al. |
| 9,452,287 B2 * | 9/2016 | Rosenbluth .......... A61N 1/0492 |
| 9,474,898 B2 | 10/2016 | Gozani et al. |
| D774,654 S | 12/2016 | Anderson |
| D778,453 S | 2/2017 | Knaus et al. |
| D779,677 S | 2/2017 | Chen |
| 9,561,397 B2 | 2/2017 | Zaki |
| D784,544 S | 4/2017 | Dudkiewicz et al. |
| D784,546 S | 4/2017 | Gordon |
| D784,946 S | 4/2017 | Jun et al. |
| D788,056 S | 5/2017 | Choi et al. |
| 9,656,070 B2 | 5/2017 | Gozani et al. |
| D789,546 S | 6/2017 | Matfus et al. |
| D789,547 S | 6/2017 | Matfus et al. |
| D791,333 S | 7/2017 | Wilson |
| D792,363 S | 7/2017 | Kim et al. |
| D794,331 S | 8/2017 | Grote |
| 9,731,126 B2 | 8/2017 | Ferree et al. |
| D801,542 S | 10/2017 | Anderson |
| D802,780 S | 11/2017 | Hsu |
| D806,669 S | 1/2018 | Kangasmaa et al. |
| D810,843 S | 2/2018 | Karvandi |
| D811,729 S | 3/2018 | Bysshe |
| D813,405 S | 3/2018 | Ho |
| D813,407 S | 3/2018 | Chen |
| D813,408 S | 3/2018 | Chen |
| D828,569 S | 9/2018 | Mercuro |
| D829,182 S | 9/2018 | Li |
| 10,076,662 B2 | 9/2018 | Tuan |
| D830,565 S | 10/2018 | Xu |
| D831,017 S | 10/2018 | Choe et al. |
| D831,221 S | 10/2018 | Smith |
| D831,335 S | 10/2018 | Crease |
| D832,230 S | 10/2018 | Lee et al. |
| D834,719 S | 11/2018 | Theriot et al. |
| D836,788 S | 12/2018 | Peng |
| 2002/0010497 A1 | 1/2002 | Merfeld et al. |
| 2003/0023192 A1 | 1/2003 | Foxlin |
| 2003/0074037 A1 | 4/2003 | Moore et al. |
| 2003/0114892 A1 | 6/2003 | Nathan et al. |
| 2003/0208246 A1 | 11/2003 | Kotlik et al. |
| 2004/0122483 A1 | 6/2004 | Nathan et al. |
| 2005/0059903 A1 | 3/2005 | Izumi |
| 2005/0080463 A1 | 4/2005 | Stahmann et al. |
| 2006/0052788 A1 | 3/2006 | Thelen et al. |
| 2006/0085049 A1 | 4/2006 | Cory et al. |
| 2006/0089683 A1 | 4/2006 | Hagglof et al. |
| 2006/0095088 A1 | 5/2006 | De Ridder |
| 2006/0173507 A1 | 8/2006 | Mrva et al. |
| 2006/0190057 A1 | 8/2006 | Reese |
| 2007/0060922 A1 | 3/2007 | Dreyfuss |
| 2007/0276449 A1 | 11/2007 | Gunter et al. |
| 2008/0077192 A1 | 3/2008 | Harry et al. |
| 2008/0146980 A1 | 6/2008 | Rousso et al. |
| 2008/0147143 A1 | 6/2008 | Popovic et al. |
| 2008/0147146 A1 | 6/2008 | Wahlgren et al. |
| 2008/0312709 A1 | 12/2008 | Volpe et al. |
| 2009/0030476 A1 | 1/2009 | Hargrove |
| 2009/0082829 A1 | 3/2009 | Panken et al. |
| 2009/0112214 A1 | 4/2009 | Philippon et al. |
| 2009/0131993 A1 | 5/2009 | Rousso et al. |
| 2009/0240303 A1 | 9/2009 | Wahlstrand et al. |
| 2009/0264789 A1 | 10/2009 | Molnar et al. |
| 2009/0270947 A1 | 10/2009 | Stone et al. |
| 2009/0326604 A1 | 12/2009 | Tyler et al. |
| 2010/0004715 A1 | 1/2010 | Fahey |
| 2010/0042180 A1 | 2/2010 | Mueller et al. |
| 2010/0057149 A1 | 3/2010 | Fahey |
| 2010/0087903 A1 | 4/2010 | Van Herk et al. |
| 2010/0094103 A1 | 4/2010 | Kaplan et al. |
| 2010/0114257 A1 | 5/2010 | Torgerson |
| 2010/0131028 A1 | 5/2010 | Hsu et al. |
| 2010/0198124 A1 | 8/2010 | Bhugra |
| 2010/0217349 A1 | 8/2010 | Fahey |
| 2010/0241464 A1 | 9/2010 | Amigo et al. |
| 2011/0066209 A1 | 3/2011 | Bodlaender et al. |
| 2011/0224665 A1 | 9/2011 | Crosby et al. |
| 2011/0257468 A1 | 10/2011 | Oser et al. |
| 2011/0264171 A1 | 10/2011 | Torgerson |
| 2011/0276107 A1 | 11/2011 | Simon et al. |
| 2011/0282164 A1 | 11/2011 | Yang et al. |
| 2012/0010680 A1 | 1/2012 | Wei et al. |
| 2012/0108998 A1 | 5/2012 | Molnar et al. |
| 2013/0096641 A1 | 4/2013 | Strother et al. |
| 2013/0158627 A1 | 6/2013 | Gozani et al. |
| 2013/0217998 A1 | 8/2013 | Mahfouz et al. |

(56) References Cited

U.S. PATENT DOCUMENTS

| | | | |
|---|---|---|---|
| 2014/0039450 | A1 | 2/2014 | Green et al. |
| 2014/0057232 | A1 | 2/2014 | Wetmore et al. |
| 2014/0081353 | A1 | 3/2014 | Cook et al. |
| 2014/0107729 | A1 | 4/2014 | Sumners et al. |
| 2014/0163444 | A1 | 6/2014 | Ingvarsson et al. |
| 2014/0245791 | A1 | 9/2014 | Proud et al. |
| 2014/0276549 | A1 | 9/2014 | Osorio |
| 2014/0296934 | A1 | 10/2014 | Gozani et al. |
| 2014/0296935 | A1 | 10/2014 | Ferree et al. |
| 2014/0309709 | A1* | 10/2014 | Gozani .............. A61N 1/36021 607/46 |
| 2014/0336730 | A1 | 11/2014 | Simon et al. |
| 2014/0379045 | A1 | 12/2014 | Rahimi et al. |
| 2015/0045853 | A1 | 2/2015 | Alataris et al. |
| 2015/0174402 | A1 | 6/2015 | Thomas et al. |
| 2015/0321000 | A1 | 11/2015 | Rosenbluth et al. |
| 2015/0328467 | A1 | 11/2015 | Demers et al. |
| 2015/0335288 | A1 | 11/2015 | Toth et al. |
| 2016/0367823 | A1 | 12/2016 | Cowan et al. |
| 2017/0209693 | A1 | 7/2017 | An et al. |
| 2018/0177996 | A1 | 6/2018 | Gozani et al. |

FOREIGN PATENT DOCUMENTS

| | | |
|---|---|---|
| CN | 102355847 | 2/2012 |
| CN | 102740919 | 10/2012 |
| DE | 102010052710 | 5/2012 |
| JP | 61-171943 | 10/1986 |
| JP | 4-347140 | 12/1992 |
| JP | 9-117453 | 5/1997 |
| JP | 2000-167067 | 6/2000 |
| JP | 2005-34402 | 2/2005 |
| JP | 2005-81068 | 3/2005 |
| JP | 2006-68300 | 3/2006 |
| JP | 418546 | 9/2008 |
| WO | WO 97/42999 | 11/1997 |
| WO | WO 99/64105 | 12/1999 |
| WO | WO 2003/051453 | 6/2003 |
| WO | WO 2004/078132 | 9/2004 |
| WO | WO 2007/061746 | 5/2007 |
| WO | WO 2008/079757 | 7/2008 |
| WO | WO 2008/088985 | 7/2008 |
| WO | WO 2011/075179 | 6/2011 |
| WO | WO 2011/137193 | 11/2011 |
| WO | WO 2012/116407 | 9/2012 |

OTHER PUBLICATIONS

Barbarisi, Manlio et al., Pregabalin and Transcutaneous Electrical Nerve Stimulation for Postherpetic Neuralgia Treatment, The Clinical Journal of Pain, Sep. 2010;26(7):567-572.

Bjordal JM et al., Transcutaneous electrical nerve stimulation (TENS) can reduce postoperative analgesic consumption. A meta-analysis with assessment of optimal treatment parameters for postoperative pain, European Journal of Pain, 2003, vol. 7(2): 181-188.

Bloodworth DM et al., Comparison of stochastic vs. conventional transcutaneous electrical stimulation for pain modulation in patients with electromyographically documented radiculopathy, American Journal of Physical Medicine & Rehabilitation, 2004, vol. 83(8): 584-591.

Chandran P et al., Development of opioid tolerance with repeated transcutaneous electrical nerve stimulation administration, Pain, 2003, vol. 102: 195-201.

Chen CC et al., A comparison of transcutaneous electrical nerve stimulation (TENS) at 3 and 80 pulses per second on cold-pressor pain in healthy human participants, Clinical Physiology and Functioning Imaging, 2010, vol. 30(4): 260-268.

Chen CC et al., An investigation into the effects of frequency-modulated transcutaneous electrical nerve stimulation (TENS) on experimentally-induced pressure pain in healthy human participants, The Journal of Pain, 2009, vol. 10(10): 1029-1037.

Chen CC et al., Differential frequency effects of strong nonpainful transcutaneous electrical nerve stimulation on experimentally induced ischemic pain in healthy human participants, The Clinical Journal of Pain, 2011, vol. 27(5): 434-441.

Chen CC et al., Does the pulse frequency of transcutaneous electrical nerve stimulation (TENS) influence hypoalgesia? A systematic review of studies using experimental pain and healthy human participants, Physiotherapy, 2008, vol. 94: 11-20.

Claydon LS et al., Dose-specific effects of transcutaneous electrical nerve stimulation on experimental pain, Clinical Journal of Pain, 2011, vol. 27(7): 635-647.

Cole, R.J. et al., Automatic Sleep/Wake Identification From Wrist Activity, Sleep, 1992, 15(5), p. 461-469.

Cruccu G. et al., EFNS guidelines on neurostimulation therapy for neuropathic pain, European Journal of Neurology, 2007, vol. 14: 952-970.

Davies HTO et al., Diminishing returns or appropriate treatment strategy?—an analysis of short-term outcomes after pain clinic treatment, Pain, 1997, vol. 70: 203-208.

Desantana JM et al., Effectiveness of transcutaneous electrical nerve stimulation for treatment of hyperalgesia and pain, Curr Rheumatol Rep. 2008, vol. 10(6): 492-499.

Dubinsky RM et al., Assessment: Efficacy of transcutaneous electric nerve stimulation in the treatment of pain in neurologic disorders (an evidence-based review): Report of the therapeutics and technology assessment subcommittee of the american academy of neurology, Neurology, 2010, vol. 74: 173-176.

Fary RE et al., Monophasic electrical stimulation produces high rates of adverse skin reactions in healthy subjects, Physiotherapy Theory and Practice, 2011, vol. 27(3): 246-251.

Fishbain, David A. et al. Does Pain Mediate the Pain Interference with Sleep Problem in Chronic Pain? Findings from Studies for Management of Diabetic Peripheral Neuropathic Pain with Duloxetine, Journal of Pain Symptom Management, Dec. 2008;36(6):639-647.

Fishbain, David A. et al., Transcutaneous Electrical Nerve Stimulation (TENS) Treatment Outcome in Long-Term Users, The Clinical Journal of Pain, Sep. 1996;12(3):201-214.

Food and Drug Administration, Draft Guidance for Industry and Staff: Class II Special Controls Guidance Document: Transcutaneous Electrical Nerve Stimulator for Pain Relief, Apr. 5, 2010.

Garrison DW et al., Decreased activity of spontaneous and noxiously evoked dorsal horn cells during transcutaneous electrical nerve stimulation (TENS), Pain, 1994, vol. 58: 309-315.

Gilron, I. et al., Chronobiological Characteristics of Neuropathic Pain: Clinical Predictors of Diurnal Pain Rhythmicity, The Clinical Journal of Pain, 2013.

Hori, T. et al., Skin Potential Activities and Their Regional Differences During Normal Sleep in Humans, The Japanese Journal of Physiology, 1970, vol. 20, p. 657-671.

Jelinek HF et al., Electric pulse frequency and magnitude of perceived sensation during electrocutaneous forearm stimulation, Arch Phys Med Rehabil, 2010, vol. 91; 1372-1382.

Jin DM et al., Effect of transcutaneous electrical nerve stimulation on symptomatic diabetic peripheral neuropathy: a meta-analysis of randomized controlled trials, Diabetes Research and Clinical Practice, 2010, vol. 89: 10-15.

Johnson MI et al., Analgesic effects of different frequencies of transcutaneous electrical nerve stimulation on cold-induced pain in normal subjects, Pain, 1989, vol. 39: 231-236.

Johnson MI et al., Transcutaneous Electrical Nerve Stimulation (TENS) and TENS-like devices: do they provide pain relief?, Pain Reviews, 2001, vol. 8: 7-44.

Johnson MI et al., Transcutaneous electrical nerve stimulation for the management of painful conditions: focus on neuropathic pain, Expert Review of Neurotherapeutics, 2011, vol. 11(5): 735-753.

Johnson; M.I. et al., An in-depth study of long-term users of transcutaneous electrical nerve stimulation (TENS). Implications for clinical use of TENS. Pain. Mar. 1991;44(3):221-229.

Kaczmarek, Kurt A. et al., Electrotactile and Vibrotactile Displays for Sensory Substitution Systems. IEEE Trans. Biomed, Eng. Jan. 1991;38 (1):1-16.

(56) References Cited

OTHER PUBLICATIONS

Kantor G et al., The effects of selected stimulus waveforms on pulse and phase characteristics at sensory and motor thresholds, Physical Therapy, 1994, vol. 74(10): 951-962.
Keller, Thierry et al., Electrodes for transcutaneous (surface) electrical stimulation. J. Automatic Control, University of Belgrade. 2008;18(2):35-45.
Koumans, A. J. R. et al., Electrodermal Levels and Fluctuations During Normal Sleep, Psychophysiology, 1968, 5(3), p. 300-306.
Kripke, D.F. et al., Wrist Actigraphic Scoring for Sleep Laboratory Patients: Algorithm Development, Journal of Sleep Research, 2010, 19(4), p. 612-619.
Law PPW et al., Optimal stimulation frequency of transcutaneous electrical nerve stimulation on people with knee osteoarthritis, J Rehabil Med, 2004, vol. 36: 220-225.
Leonard G et al., Deciphering the role of endogenous opioids in high-frequency TENS using low and high doses of naloxone, Pain, 2010, vol. 151: 215-219.
Levy et al., A comparison of two methods for measuring thermal thresholds in diabetic neuropathy, Journal of Neurology, Neurosurgery, and Psychiatry, 1989, vol. 52: 1072-1077.
Lykken, D.T., Properties of Electrodes Used in Electrodermal Measurement. J. Comp. Physiol. Psychol. Oct. 1959;52:629-634.
Lykken, D.T., Square-Wave Analysis of Skin Impedance. Psychophysiology. Sep. 1970;7(2):262-275.
Melzack R et al., Pain mechanisms: A New Theory, Science, 1965, vol. 150(3699): 971-979.
Moran F et al., Hypoalgesia in response to transcutaneous electrical nerve stimulation (TENS) depends on stimulation intensity, The Journal of Pain, 2011, vol. 12(8): 929-935.
Oosterhof, Jan et al., Outcome of transcutaneous electrical nerve stimulation in chronic pain: short-term results of a double-blind, randomised, placebo-controlled trial. J. Headache Pain. Sep. 2006;7(4):196-205.
Ocsterhof, Jan et al., The long-term outcome of transcutaneous electrical nerve stimulation in the treatment for patients with chronic pain: a randomized, placebo-controlled trial. Pain Pract. Sep. 2012;12(7):513-522.
Pantaleao MA et al., Adjusting pulse amplitude during transcutaneous electrical nerve stimulation (TENS) application produces greater hypoalgesia, The Journal of Pain, 2011, vol. 12(5): 581-590.
Paquet, J. et al., Wake Detection Capacity of Actigraphy During Sleep, Sleep, 2007, 30(10), p. 1362-1369.
Pieber K et al., Electrotherapy for the treatment of painful diabetic peripheral neuropathy: a review, Journal of Rehabilitation Medicine, 2010, vol. 42: 289-295.
Raskin, J. et al., A Double-Blind, Randomized Multicenter Trial Comparing Duloxetine with Placebo in the Management of Diabetic Peripheral Neuropathic Pain, Pain Medicine, 2005, 6(5), p. 346-356.
Sadeh, A., The Role and Validity of Actigraphy in Sleep Medicine: An Update, Sleep Medicine Reviews, 2011, vol. 15, p. 259-267.
Sadosky, A. et al., Burden of Illness Associated with Painful Diabetic Peripheral Neuropathy Among Adults Seeking Treatment in the US: Results from a Retrospective Chart Review and Cross-Sectional Survey, Diabetes, Metabolic Syndrome and Obesity: Targets and Therapy, 2013, vol. 6. p. 79-92.
Scherder, E. J. A. et al., Transcutaneous Electrical Nerve Stimulation (TENS) Improves the Rest-Activity Rhythm in Midstage Alzheimer's Disease, Behavioral Brain Research, 1999, vol. 101, p. 105-107.
Tryon, W. W., Issues of Validity in Actigraphic Sleep Assessment, Sleep, 2004, 27(1), p. 158-165.
Tsai, Y. et al., Impact of Subjective Sleep Quality on Glycemic Control in Type 2 Diabetes Mellitus, Family Practice, 2012, vol. 29, p. 30-35.
Van Boxtel, A., Skin resistance during square-wave electrical pulses of 1 to 10 mA. Med. Biol. Eng. Comput. Nov. 1977;15(6):679-687.
Van Someren, E. J. W. et al., Gravitational Artefact in Frequency Spectra of Movement Acceleration: Implications for Actigraphy in Young and Elderly Subjects, Journal of Neuroscience Methods, 1996, vol. 65, p. 55-62.
Webster, J. B. et al., An Activity-Based Sleep Monitor System for Ambulatory Use, Sleep, 1982, 5(4), p. 389-399.
Zelman, D. C. et al., Sleep Impairment in Patients With Painful Diabetic Peripheral Neuropathy, The Clinical Journal of Pain, 2006, 22(8), p. 681-685.
Aurora, R. et al., The Treatment of Restless Legs Syndrome and Periodic Limb Movement Disorder in Adults—An Update for 2012: Practice Parameters with an Evidence-Based Systematic Review and Meta-Analyses, Sleep, 2012, vol. 35, No. 8, p. 1039-1062.
Bonnet, M. et al., Recording and Scoring Leg Movements, Sleep, 1993, vol. 16, No. 8, p. 748-759.
Boyle, J. et al., Randomized, Placebo-Controlled Comparison of Amitriptyline, Duloxeline, and Pregabalin in Patients With Chronic Diabetic Peripheral Neuropathic Pain, Diabetes Care, 2012, vol. 35, p. 2451-2458.
Kovacevic-Ristanovic, R. et al., Nonpharmacologic Treatment of Periodic Leg Movements in Sleep, Arch. Phys. Med. Rehabil., 1991, vol. 72, p. 385-389.
Lopes, L. et al., Restless Legs Syndrome and Quality of Sleep in Type 2 Diabetes, Diabetes Care, 2005, vol. 28, No. 11, p. 2633-2636.
Nightingale, S., The neuropathic pain market. Nature Reviews, 2012, vol. 11, p. 101-102.
Zucconi, M. et al., The official World Association of Sleep Medicine (WASM) standards for recording and scoring periodic leg movements in sleep (PLMS) and wakefulness (PLMW) developed in collaboration with a task force from the International Restless Legs Syndrome Study Group (IRLSSG), Sleep Medicine, 2006, vol. 7, p. 175-183.
Sheridan et al., Some Factors Influencing the Threshold of the Electrocutaneous Stimulus, Perceptual and Motor Skills, 1966, vol. 22, pp. 647-654.
Susi, M. et al., Motion Mode Recognition and Step Detection Algorithms for Mobile Phone Users, Sensors, vol. 13, 2013, pp. 1539-1562.
Amazon, "Quell 2.0 Wearable Pain Relief Technology", Sep. 15, 2018. http://www.amazon.com/Quell-Wearable-Pain-Relief-Technology/dp/B07DHW2MJJ/ref=cm_cr_arp_d_product_top?ie=UTF8. Shown on p. 1. (Year: 2018).
Amazon, "Quell Wearable Pain Relief Technology Starter Kit", Oct. 18, 2017. http://www.amazon.com/Quell-Wearable-ReliefTechnology-Starter/dp/B075YVCLZT/ref=cm_cr_arp_d_product_top?ie=UTF8. Shown on p. 1. (Year: 2017).

\* cited by examiner

APPARATUS AND METHOD FOR AUTOMATED COMPENSATION OF TRANSCUTANEOUS ELECTRICAL NERVE STIMULATION FOR TEMPORAL FLUCTUATIONS SUCH AS CIRCADIAN RHYTHMS

REFERENCE TO PENDING PRIOR PATENT APPLICATIONS

This patent application:

(i) is a continuation-in-part of pending prior U.S. patent application Ser. No. 14/253,628, filed Apr. 15, 2014 by Neurometrix, Inc. and Shai Gozani et al. for TRANSCUTANEOUS ELECTRICAL NERVE STIMULATOR WITH AUTOMATIC DETECTION OF USER SLEEP-WAKE STATE; and (ii) claims benefit of prior U.S. Provisional Patent Application Ser. No. 62/361,698, filed Jul. 13, 2016 by NeuroMetrix, Inc. and Shai N. Gozani for APPARATUS AND METHOD FOR AUTOMATED COMPENSATION OF TRANSCUTANEOUS ELECTRICAL NERVE STIMULATION FOR CIRCADIAN RHYTHMS, which patent application is hereby incorporated herein by reference.

FIELD OF THE INVENTION

This invention generally relates to Transcutaneous Electrical Nerve Stimulation (TENS) devices that deliver electrical currents across the intact skin of a user in order to provide symptomatic relief of chronic pain, and more particularly to TENS devices configured for automated compensation for circadian rhythms and other temporal variations in the user's physiology.

BACKGROUND OF THE INVENTION

Transcutaneous electrical nerve stimulation (TENS) is the delivery of electricity (i.e., electrical stimulation) across the intact surface of a user's skin in order to activate sensory nerve fibers. The most common application of TENS therapy is to provide analgesia, such as for chronic pain. Other applications of TENS therapy include, but are not limited to, reducing the symptoms of restless leg syndrome, decreasing nocturnal muscle cramps, and providing relief from generalized pruritis. A conceptual model for how sensory nerve stimulation leads to pain relief was proposed by Melzack and Wall in 1965. Their theory stipulates that activation of sensory nerves (Aβ fibers) closes a "pain gate" in the spinal cord that inhibits the transmission of pain signals carried by nociceptive afferents (C and Aδ fibers) to the brain. In the past 20 years, anatomic pathways and molecular mechanisms that may underlie the pain gate have been identified. Sensory nerve stimulation (e.g., via TENS) activates the descending pain inhibition system, primarily the periaqueductal gray (PAG) and rostroventral medial medulla (RVM) located in the midbrain and medulla sections of the brainstem, respectively. The PAG has neural projections to the RVM, which in turn has diffuse bilateral projections into the spinal cord dorsal horn that inhibit ascending pain signal transmission.

TENS is typically delivered in short discrete pulses (with each pulse typically being several hundred microseconds in duration) at frequencies between about 10 and 150 Hz, through hydrogel electrodes placed on the user's body. TENS is characterized by a number of electrical parameters including the amplitude and shape of the stimulation pulse (which combine to establish the pulse charge), the frequency and pattern of the pulses, the duration of a therapy session and the interval between therapy sessions. All of these parameters are correlated to the therapeutic dose. For example, higher amplitude and longer pulses (i.e., larger pulse charge) increase the dose, whereas shorter therapy sessions decrease the dose. Clinical studies suggest that pulse charge and therapy session duration have the greatest impact on therapeutic dose.

To achieve maximum pain relief (i.e., hypoalgesia), TENS needs to be delivered at an adequate stimulation intensity. Intensities below the threshold of sensation are not clinically effective. The optimal therapeutic intensity is often described as one that is "strong yet comfortable". Most TENS devices rely on the user to set the stimulation intensity, usually through a manual intensity control comprising an analog intensity knob or digital intensity control pushbuttons. In either case (i.e., analog control or digital control), the user must manually increase the intensity of the stimulation to what the user believes to be a therapeutic level. Therefore, a major limitation of current TENS devices is that it may be difficult for many users to determine an appropriate therapeutic stimulation intensity. As a result, the user will either require substantial support from medical staff or they may fail to get pain relief due to an inadequate stimulation level.

A newly-developed wearable TENS device (Quell®, Neurometrix, Inc., Waltham, Mass., USA) uses a novel method for calibrating the stimulation intensity in order to maximize the probability that the TENS stimulation intensity will fall within the therapeutic range. With the Quell® device, the user identifies their electrotactile sensation threshold and then the therapeutic intensity is automatically estimated by the TENS device based on the identified electrotactile sensation threshold.

Pain relief from TENS stimulation usually begins within 15 minutes of the stimulation onset and may last up to an hour following the completion of the stimulation period (also known as a "therapy session"). Each therapy session typically runs for 30-60 minutes. To maintain pain relief (i.e., hypoalgesia), TENS therapy sessions typically need to be initiated at regular intervals. Newly-developed wearable TENS devices, such as the aforementioned Quell® device, provide the user with an option to automatically restart therapy sessions at pre-determined time intervals.

The persistent nature of chronic pain and the convenience of "wear-and-forget" TENS technology may lead some users to wear the TENS device daily for an extended period of time. To achieve maximum pain relief, TENS needs to be delivered at an adequate stimulation intensity level throughout the day and also at night (i.e., when the user is asleep). The optimal therapeutic stimulation intensity level varies from person to person, and depends upon the electrotactile threshold of each individual user. Once the optimal setting for the therapeutic stimulation intensity level is determined for a particular user, it remains fixed for that user for all subsequent TENS therapeutic sessions throughout the day.

However, all organisms have internal "clocks" that regulate normal biological processes and normal physiological function. The most important and well understood internal "clock" is the circadian rhythm. In the absence of external entrainment cues, the human circadian rhythm has a 20 to 28 hour cycle. The circadian oscillator is synchronized to the physical 24-hour day-night cycle by environmental signals such as light. Therefore, a single time-invariant TENS dose may not provide consistent pain relief throughout the day for a TENS user.

A growing recognition of the importance of the circadian rhythm, and other temporal fluctuations, in various diseases and the efficacy of their treatments has led to the concept of "chronotherapy," which is an attempt to design therapeutic approaches that account for the temporal properties of human physiological function. By way of example but not limitation, circadian rhythms influence chronic pain and may impact the treatment of pain using TENS therapy. Variations in pain intensity over the course of the day are common. Some pain conditions, such as painful diabetic neuropathy, exhibit peak intensity (i.e., the greatest level of pain) in the evening, while other pain conditions, such as fibromyalgia, exhibit peak intensity (i.e., the greatest level of pain) in the morning. One significant implication of these fluctuations in the degree of pain experienced by the user over the course of the day is that a user may require a higher therapeutic dose (i.e., a higher level of TENS stimulation) at certain times of the day in order to achieve optimal and stable pain control.

A user's sensory threshold may vary over the course of the day, which may also impact the efficacy of TENS therapy at a given stimulation intensity level. In other words, the threshold at which a sensory stimulus (e.g., electrical stimulation, light, heat, etc.) is detected by the user is not constant, but varies over the course of the 24-hour cycle. Although, circadian variation in the perception threshold to electrical stimulation, commonly referred to as the "electrotactile threshold", has not been studied extensively, several published studies suggest that humans experience time-varying perception thresholds to electrical stimulation (e.g., TENS therapy). Most users experience their lowest perception threshold (i.e., greatest sensitivity) to electrical stimulation (e.g., TENS therapy) in the late afternoon and early evening (see, for example, Sheriden et al., "Some Factors Influencing the Threshold of the Electrocutaneous Stimulus". Percept. Mot. Skills, 1966). However, there is substantial inter-individual variation and some users experience a minimum perception threshold at other times of the day. The implication of a varying electrotactile perception threshold is that the therapeutic effect of TENS stimulation therapy may vary in a circadian fashion if the stimulation intensity is held constant throughout the day. More particularly, if the user's electrotactile perception threshold is low, then more sensory nerves will be stimulated as compared to when the user's electrotactile perception threshold is high.

The anatomical location where circadian modulation occurs may be in the periphery of the user's body, in the user's central nervous system (CNS), or both. In the periphery of the user's body, modulation of nerve stimulation may be due to changes in body surface temperature, biophysical changes in peripheral nerve membranes, and other effects. Circadian rhythms may also modulate sensory perception in the CNS where the integration of peripheral sensory signals may be amplified or attenuated in a time-varying fashion. Regardless of the site(s) of circadian control/modulation of the electrotactile perception threshold, the net effect is that the sensory input that triggers the descending pain inhibition system fluctuates in a rhythmic fashion, leading to an oscillation in the effective stimulation intensity. To maintain stable and uniform therapeutic effectiveness of TENS therapy for a particular user, the circadian rhythms of that particular user can be exploited in order to optimally regulate TENS stimulation parameters, with the goal of enhancing TENS therapeutic effectiveness by counteracting the time-dependent nature of the sensory perception threshold and pain level.

SUMMARY OF THE INVENTION

The present invention comprises the provision and use of a novel TENS device which comprises a stimulator designed to be placed on a user's upper calf (or other anatomical location) and a pre-configured electrode array designed to provide electrical stimulation to at least one nerve disposed in the user's upper calf (or other anatomical location). A key feature of the present invention is that the novel TENS device automatically adjusts stimulation parameters according to the time of day in order to compensate for circadian rhythms and other temporal variations in the user's physiology.

In one preferred form of the present invention, there is provided apparatus for transcutaneous electrical nerve stimulation in a user, the apparatus comprising:
  stimulation means for electrically stimulating at least one nerve with at least one stimulation pulse;
  control means connected to said stimulation means for controlling at least one characteristic of said at least one stimulation pulse; and
  modulating means connected to the control means for modulating said at least one characteristic of said at least one stimulation pulse according to the time of day.

In another preferred form of the present invention, there is provided a method for controlling transcutaneous electrical nerve stimulation based on the time of day, the method comprising the steps of:
  providing apparatus for transcutaneous electrical nerve stimulation in a user, the apparatus comprising:
    stimulation means for electrically stimulating at least one nerve with at least one stimulation pulse;
    control means connected to said stimulation means for controlling at least one characteristic of said at least one stimulation pulse; and
    modulating means connected to the control means for modulating said at least one characteristic of said at least one stimulation pulse;
  determining a time-varying function within a 24-hour period;
  using said stimulation means to electrically stimulate at least one nerve; and
  modulating at least one characteristic of said electrical stimulation according to the time of day and said time-varying function.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The present invention comprises the provision and use of a novel TENS device which comprises a stimulator designed to be placed on a user's upper calf (or other anatomical location) and a pre-configured electrode array designed to provide electrical stimulation to at least one nerve disposed in the user's upper calf (or other anatomical location). A key feature of the present invention is that the novel TENS device automatically adjusts stimulation parameters according to the time of day.

Figure 1:
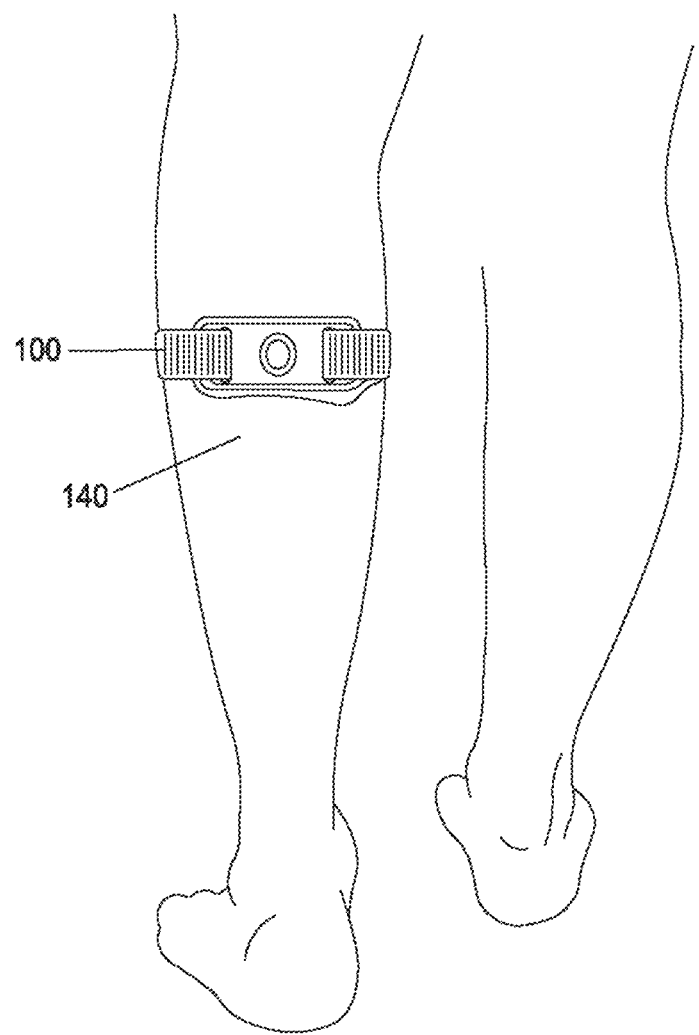
FIG. 1 is a schematic view showing a novel TENS device formed in accordance with the present invention, wherein the novel TENS device is mounted to the upper calf of a user.

More particularly, and looking now at FIG. 1, there is shown a novel TENS device 100 formed in accordance with the present invention, with novel TENS device 100 being shown worn on a user's upper calf 140. A user may wear TENS device 100 on one leg or on both legs (either one at a time or simultaneously) or a user may wear a TENS device 100 on another area of the body, separate from, or in addition to, a TENS device worn on one leg (or both legs) of the user.

Figure 2:
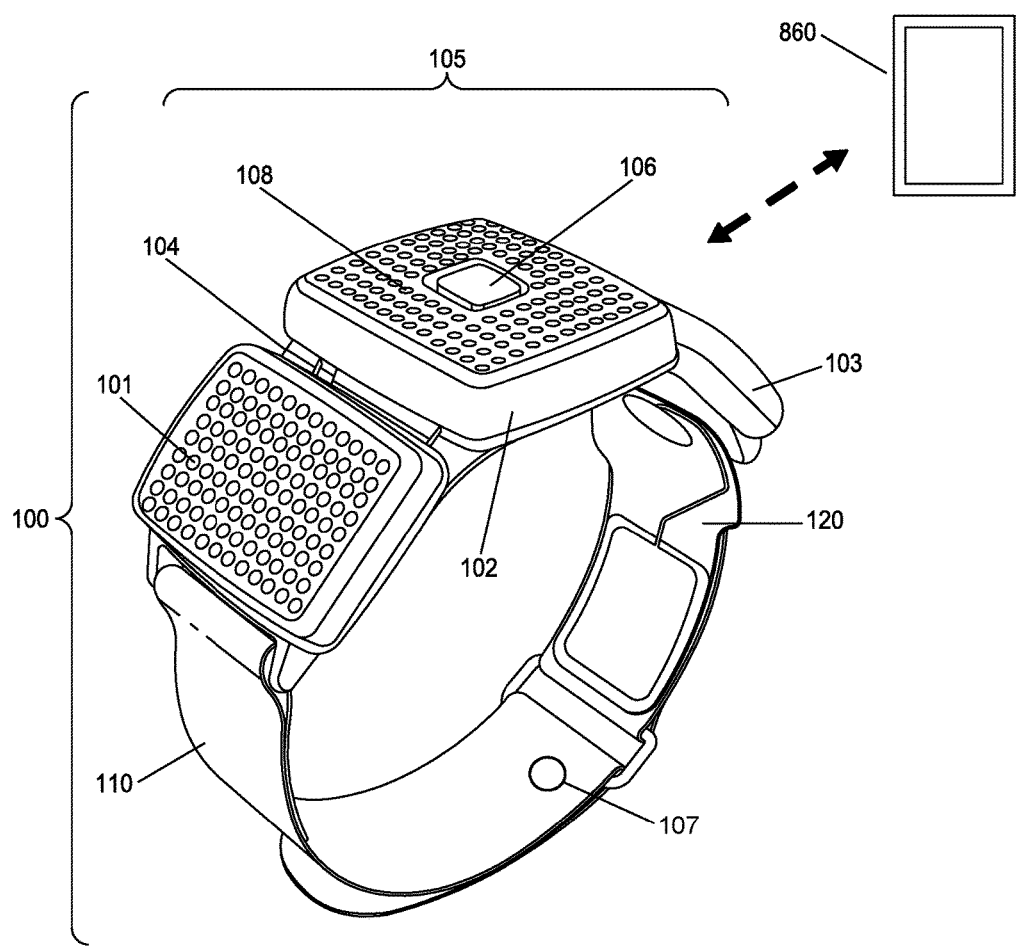
FIG. 2 is a schematic view showing the novel TENS device of FIG. 1 in greater detail.

Looking next at FIG. 2, TENS device 100 is shown in greater detail. TENS device 100 preferably comprises three primary components: a stimulator 105, a strap 110, and an electrode array 120 (comprising a cathode electrode and an anode electrode appropriately connected to stimulator 105 as is well known in the art). As shown in FIG. 2, stimulator 105 generally comprises three mechanically and electrically inter-connected compartments 101, 102, and 103. Compartments 101, 102, 103 are preferably inter-connected by hinge mechanisms 104 (only one of which is visible in FIG. 2), thereby allowing TENS device 100 to conform to the curved anatomy of a user's leg. In a preferred embodiment of the present invention, compartment 102 houses the TENS stimulation circuitry (except for a battery) and user interface elements 106 and 108. Compartment 102 also houses an accelerometer 172 (see FIG. 4), preferably in the form of a MEMS digital accelerometer microchip (e.g., Freescale MMA8451Q), for detecting user gestures such as taps to the central compartment 102, user leg and body orientation, and user leg and body motion. Compartment 102 also houses a real-time clock 505 (FIG. 4) and a temperature sensor 107 (FIG. 4) for measuring the user's skin surface temperature. In one preferred form of the present invention, compartments 101 and 103 are smaller, auxiliary compartments that house a battery for powering the TENS stimulation circuitry and other circuitry, and other ancillary elements, such as an ambient light sensor or detector 510 (FIG. 4) for determining ambient light conditions, and a wireless interface unit (not shown) of the sort well known in the art for allowing TENS device 100 to wirelessly communicate with other elements (e.g., a hand-held electronic device such as a smartphone 860). In another form of the present invention, only one or two compartments may be used for housing all the TENS stimulation circuitry, battery, and other ancillary elements of the present invention. In another form of the present invention, a greater number of compartments are used, e.g., to conform better to the body and to improve user comfort. And in still another form of the present invention, a flexible circuit board is used to distribute the TENS stimulation circuitry and other circuitry more evenly around the leg and thereby reduce thickness.

As discussed above, temperature sensor 107 is preferably disposed within compartment 102 of stimulator 105. However, it should be appreciated that, if desired, temperature sensor 107 may be embedded in the strap 110 (e.g., in the manner shown in FIG. 2) in order to measure the user's skin temperature, with the temperature measurement being electrically communicated to stimulator 105 (e.g., wirelessly or via a lead embedded in strap 110, not shown).

Still looking at FIG. 2, interface element 106 preferably comprises a push button for user control of electrical stimulation by TENS device 100, and interface element 108 preferably comprises an LED for indicating stimulation status and providing other feedback to the user. Although a single LED is shown, interface element 108 may comprise multiple LEDs with different colors. Additional user interface elements (e.g., an LCD display, audio feedback through a beeper or voice output, haptic devices such as a vibrating element, a smartphone running an appropriate app, etc.) are also contemplated and are within the scope of the present invention.

In one preferred form of the invention, TENS device 100 is configured to be worn on the user's upper calf 140 as shown in FIG. 1 (although it should be appreciated that TENS device 100 may be worn on other anatomical locations or multiple TENS devices 100 may be worn on various anatomical locations, etc.). TENS device 100 (comprising stimulator 105, electrode array 120, and strap 110) is secured to upper calf 140 (or other anatomical location) of the user by placing the apparatus in position and then tightening strap 110. More particularly, in one preferred form of the invention, electrode array 120 is deliberately sized and configured so that it will apply appropriate electrical stimulation to the appropriate anatomy of the user regardless of the specific rotational position of TENS device 100 on the leg (or other anatomical location) of the user. Although the preferred embodiment of the present invention comprises placement of the TENS device on the upper calf of the user, additional locations (such as above the knee, on an upper extremity, etc.) are also contemplated and are considered to be within the scope of the present invention. Furthermore, it is also contemplated that the TENS device may be placed on other anatomical locations of the user, e.g., the lower back of the user (however, it will be appreciated that in some of these alternative anatomical locations, electrode array 120 may not be able to supply appropriate electrical stimulation to the appropriate anatomy of the user regardless of the specific rotational position of the TENS device 100 on the anatomy of the user).

Figure 3:
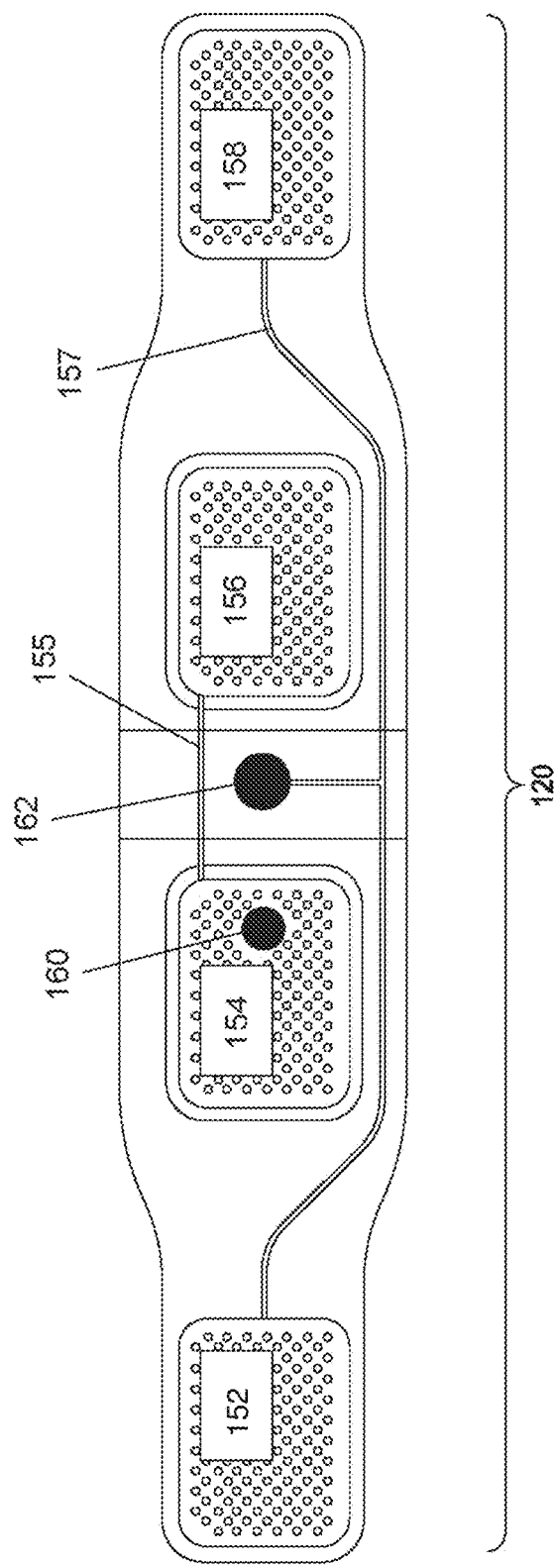
FIG. 3 is a schematic view showing the electrode array of the novel TENS device of FIGS. 1 and 2 in greater detail.

FIG. 3 shows a schematic view of one preferred embodiment of electrode array 120. Electrode array 120 preferably comprises four discrete electrodes 152, 154, 156, 158, each having an equal or similar size (i.e., an equal or similar size surface area). Electrodes 152, 154, 156, 158 are preferably connected in pairs so that electrodes 154 and 156 (representing the cathode of TENS device 100) are electrically connected to one another (e.g., via connector 155), and so that electrodes 152 and 158 (representing the anode of TENS device 100) are electrically connected to one another (e.g., via connector 157). It should be appreciated that electrodes 152, 154, 156, 158 are preferably appropriately sized, and connected in pairs, so as to ensure adequate skin coverage regardless of the rotational position of TENS device 100 (and hence regardless of the rotational position of electrode array 120) on the leg (or other anatomical location) of a user. Furthermore, it should be appreciated that electrodes 152, 154, 156, 158 are not connected in an interleaved fashion, but rather are connected so that the two inside electrodes 154, 156 are connected to one another, and so that the two outside electrodes 152, 158 are connected to one another. This electrode connection pattern ensures that if the two outer electrodes 152, 158 should inadvertently come into contact with one another, an electrical short of the stimulation current flowing directly from cathode to anode will not occur (i.e., the electrode connection pattern ensures that the therapeutic TENS current is always directed through the tissue of the user).

Figure 4:
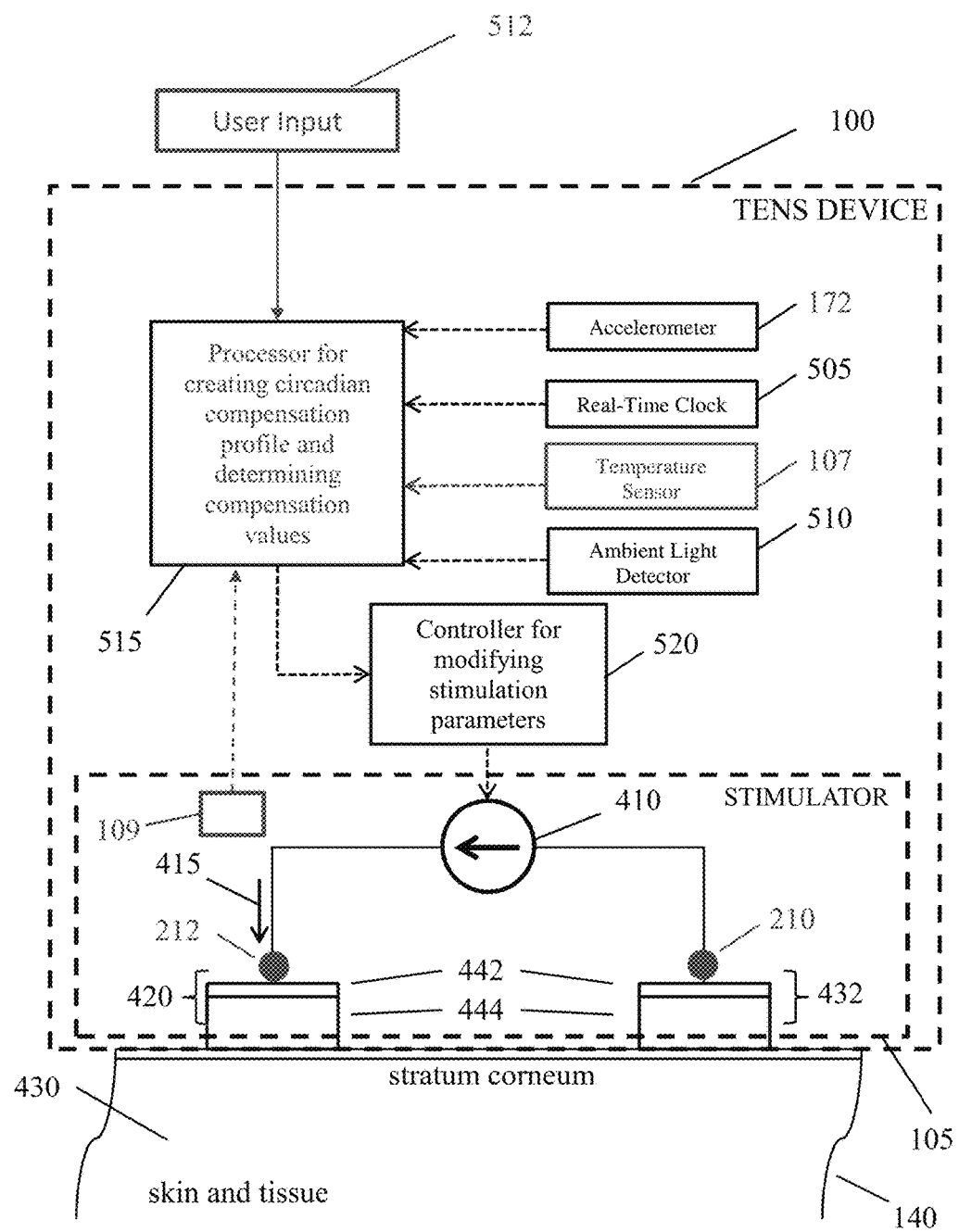
FIG. 4 is a schematic view of the novel TENS device of FIGS. 1-3, including its circadian compensation processor for creating compensation profiles and determining compensation values.

Electrical current (i.e., for therapeutic electrical stimulation to the tissue) is provided to the electrode pairs 154, 156 and 152, 158 by connectors 160, 162 which mate with complementary connectors 210, 212, respectively, on stimulator 105 (see FIG. 4). Stimulator 105 generates electrical currents that are passed through electrodes 154, 156 and electrodes 152, 158 via connectors 160, 162, respectively.

In one preferred embodiment of the present invention, the skin-contacting conductive material of electrodes 152, 154, 156, 158 is a hydrogel material which is "built into" electrodes 152, 154, 156, 158. The function of the hydrogel material on the electrodes is to serve as an interface between the electrodes 152, 154, 156, 158 and the skin of the user (i.e., within, or adjacent to, or proximal to, the portion of the user's body in which the sensory nerves which are to be stimulated reside). Other types of electrodes such as dry electrodes and non-contact stimulation electrodes have also been contemplated.

FIG. 4 is a schematic representation of the current flow between TENS device 100 and the user. As seen schematically in FIG. 4, stimulation current 415 from a constant current source 410 flows into the user's tissue 430 (e.g., the user's upper calf) via an anode electrode 420 (which anode electrode 420 comprises the aforementioned electrodes 152, 158). Anode electrode 420 comprises a conductive backing (e.g., silver hatch) 442 and hydrogel 444. The current passes through the user's tissue 430 and returns to constant current source 410 through cathode electrode 432 (which cathode electrode 432 comprises the aforementioned electrodes 154, 156). Cathode electrode 432 also comprises a conductive backing 442 and hydrogel 444. Constant current source 410 preferably provides an appropriate biphasic waveform (i.e., biphasic stimulation pulses) of the sort well known in the art of TENS therapy. In this respect it should be appreciated that the designation of "anode" and "cathode" electrodes is purely notational in the context of a biphasic waveform (i.e., when the biphasic stimulation pulse reverses its polarity in its second phase of the biphasic TENS stimulation, current will be flowing into the user's body via "cathode" electrode 432 and out of the user's body via "anode" electrode 420).

Figure 5:
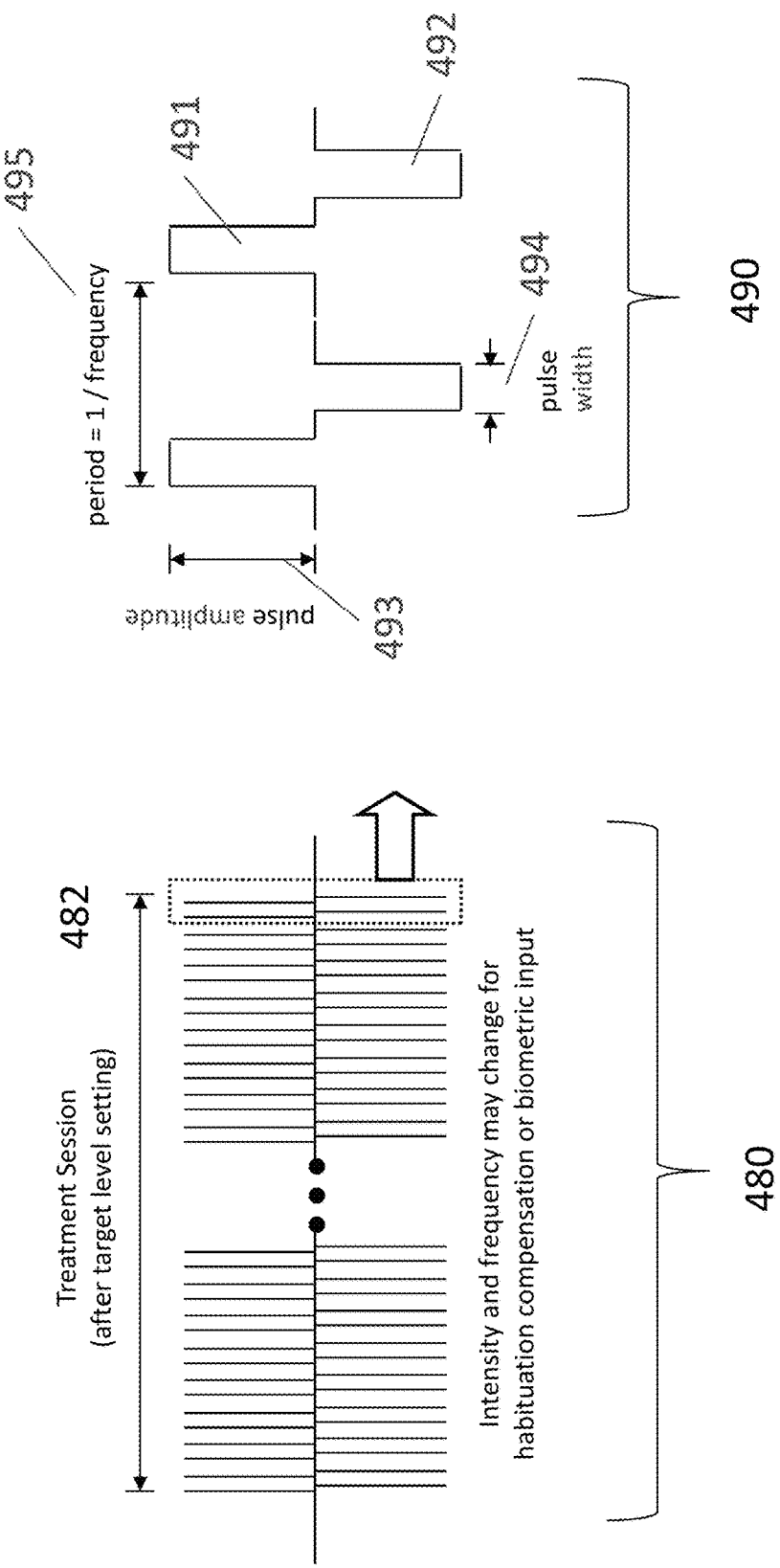
FIG. 5 is a schematic view showing the stimulation pulse train generated by the stimulator of the novel TENS device of FIGS. 1-4.

FIG. 5 is a schematic view showing a pulse train 480 provided by stimulator 105 during a TENS therapy session, and the waveform of two individual pulses 490. In one form of the invention, each pulse waveform is charge-balanced for two phases 491 and 492 of the pulse which prevents iontophoretic build-up under the electrodes of the electrode array 120 that can lead to skin irritation and potential skin damage. In another form of the invention, the individual pulses are unbalanced, however, charge-balancing is achieved across multiple consecutive pulses. Pulses of fixed or randomly varying frequencies persist throughout the duration of the therapy session 482. The intensity of the stimulation (i.e., the amplitude 493 of the current delivered by stimulator 105) is adjusted in response to user input and for habituation compensation, as will hereinafter be discussed in further detail.

In prior U.S. patent application Ser. No. 13/678,221, filed Nov. 15, 2012 by Neurometrix, Inc. and Shai N. Gozani et al. for APPARATUS AND METHOD FOR RELIEVING PAIN USING TRANSCUTANEOUS ELECTRICAL NERVE STIMULATION, issued as U.S. Pat. No. 8,948,876 on Feb. 3, 2015, which patent is hereby incorporated herein by reference, apparatus and methods are disclosed for allowing a user to personalize TENS therapy stimulation intensity according to the electrotactile perception threshold of the user at the time of the setup of the TENS device. U.S. Pat. No. 8,948,876 also discloses apparatus and methods to automatically restart additional therapy sessions after an initial manual start by the user. In prior U.S. patent application Ser. No. 14/230,648, filed Mar. 31, 2014 by NeuroMetrix, Inc. and Shai Gozani et al. for DETECTING CUTANEOUS ELECTRODE PEELING USING ELECTRODE-SKIN IMPEDANCE, issued as U.S. Pat. No. 9,474,898 on Oct. 25, 2016, which patent is hereby incorporated herein by reference, apparatus and methods are disclosed which allow safe delivery of TENS therapies at night when the user is asleep. These methods and apparatus allow the TENS device to be worn by a user for an extended period of time, including 24 hours a day.

A fixed TENS stimulation level may not be appropriate to deliver consistently comfortable and effective pain relief to a user throughout both the day and the night, since the impact of circadian or other time-varying rhythms mitigates the effectiveness of TENS stimulation. Parameters impacting TENS stimulation effectiveness include, but are not limited to, stimulation pulse amplitude 493 and pulse width 494, pulse frequency 495, and therapy session duration 482. By way of example but not limitation, higher amplitude and longer pulses (i.e., larger pulse charge) increase the stimulation delivered to the user (i.e., the stimulation "dose"), whereas shorter therapy sessions decrease stimulation delivered to the user (i.e., the stimulation "dose"). Clinical studies suggest that pulse charge (i.e., pulse amplitude and pulse width) and therapy session duration have the greatest impact on the therapeutic stimulation delivered to the user (i.e., the therapeutic stimulation "dose").

Figure 6:
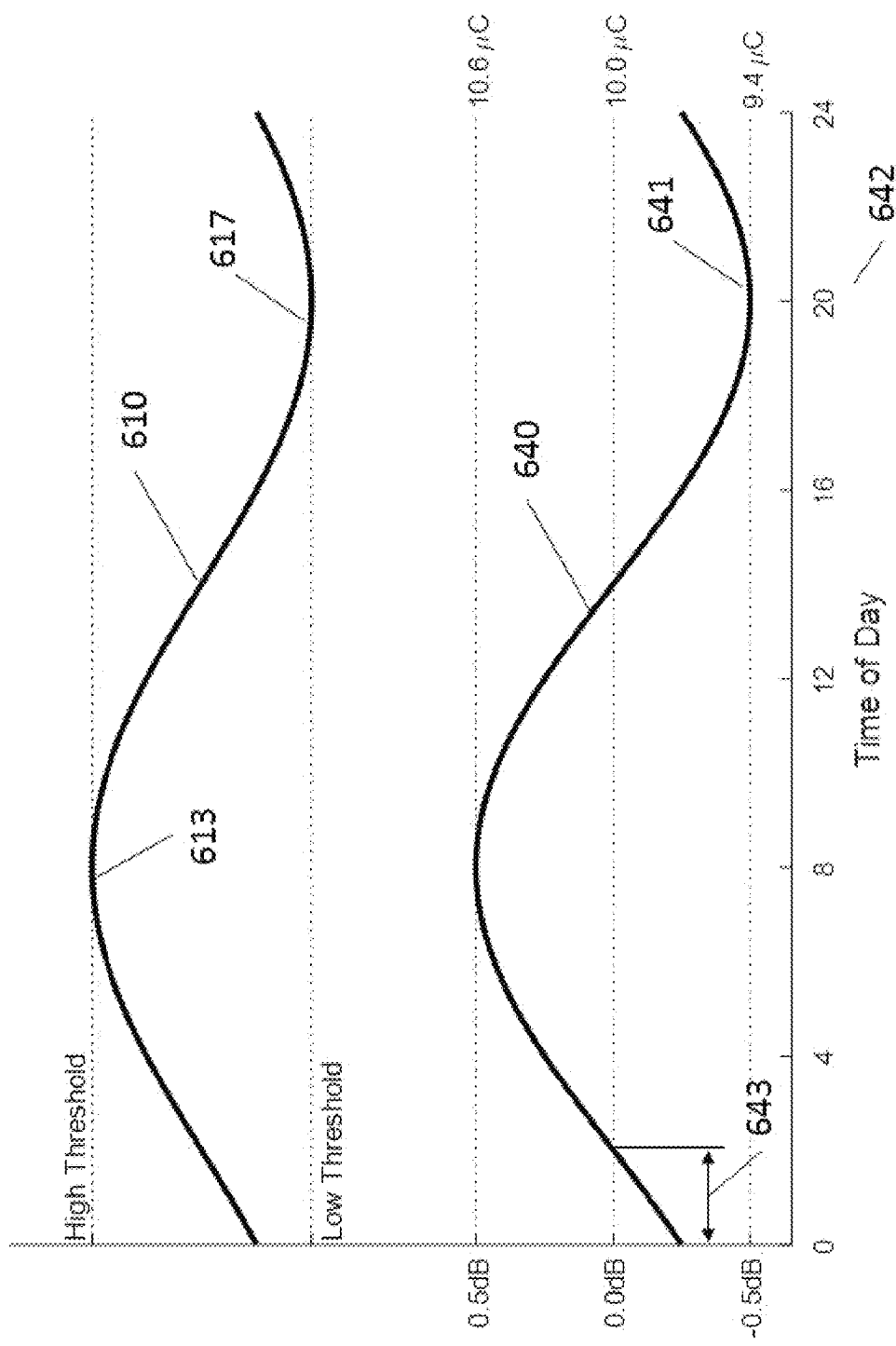
FIG. 6 is a schematic view showing exemplary circadian fluctuation in the electrotactile perception threshold and a matching circadian compensation function for regulating the stimulation pulse intensity delivered to a user by the novel TENS device of FIGS. 1-4.

One object of the present invention is to permit TENS device 100 to automatically offset the impact of circadian or other time-varying rhythms on the comfort and efficacy of TENS stimulation therapy, where efficacy is usually considered to be analgesia (i.e., the alleviation of pain) but may also be viewed more broadly in terms of other clinical effects of TENS such as, but not limited to, therapy for sleep disorders, therapy for muscle cramps, and therapy for treating pruritis. More particularly, the present invention automatically modulates at least one TENS stimulation parameter in order to compensate for the effect of at least one circadian rhythm. By way of example but not limitation, as previously discussed, it is known that an individual's electrotactile perception threshold varies over the course of a day in a circadian fashion. FIG. 6 shows an example of the circadian fluctuation in the electrotactile perception threshold 610 for an exemplary user over the course of a day. If constant electrical parameters are used throughout the day, then at times when the elecrotactile perception threshold is low (617), e.g., during the early evening, the user may perceive a strong and potentially uncomfortable electrical stimulation when stimulated by TENS device 100. Conversely, when the electrotactile perception threshold is high (613), e.g., during the morning, the user may perceive a weak and potentially therapeutically sub-optimal electrical stimulation. In order to avoid differences in user perception regarding stimulation intensity which can result from circadian fluctuation in the user's electrotactile perception threshold, in one preferred form of the present invention, TENS device 100 is configured to automatically adjust TENS stimulation parameters (e.g., pulse amplitude, pulse length, etc.) so that the user experiences consistently comfortable and therapeutically effective stimulation throughout the entire day. In another form of the invention, TENS device 100 is configured to automatically adjust TENS stimulation parameters (e.g., pulse amplitude, pulse length, etc.) in order to account for circadian fluctuations in the user's pain level. In another form of the invention, TENS device 100 is configured to provide adjusted TENS stimulation (i.e., by adjusting one or more TENS stimulation parameters) which is appropriate for a specific time of day, such as adjusting different stimulation parameters in the daytime periods and the nighttime periods.

In one preferred form of the present invention, the modulated stimulation parameters are pulse amplitude 493 and pulse width 494, or a combination of pulse amplitude 493 and pulse width 494 (pulse charge), since these stimulation parameters are known to have a direct impact on both comfort and analgesic efficacy. In another form of the invention, the modulated stimulation parameter is the pulse frequency 495. In yet another form of the invention, the modulated stimulation parameter is the duration of the therapy session 482. In another form of the invention, the modulated stimulation parameter is the elapsed time between consecutive therapy sessions. Modulation of other stimulation parameters, or combinations of stimulation parameters, falls within the scope of the present invention. By way of example but not limitation, in one form of the invention, the pulse charge and the pulse frequency are concurrently regulated in order to compensate for one or more circadian rhythms.

In one preferred form of the invention, the automatic compensation for temporal fluctuations (i.e., the automatic modulation of one or more stimulation parameters) is accomplished through a time-dependent function that offsets the actual stimulation intensity delivered to the user by TENS device 100. In the case of a circadian rhythm, this compensation is sometimes hereinafter called a circadian compensation function (CCF). The CCF modulates an electrical stimulation parameter during TENS therapy so as to offset the effect of a circadian rhythm on TENS therapy. In a preferred form of the invention, the stimulation parameter p(t) is modulated by a time-varying factor $\Delta(t)$, as described by Equation 1, $$\Delta(t)=A \sin(\omega t-\delta) \quad \text{Eq. 1}$$

where $\omega$ is the angular frequency of the circadian rhythm. In the preferred embodiment, we assume that the user has a normal circadian rhythm that is entrained to the day night 24-hour cycle (86,400 seconds). Therefore, the angular frequency is $2\pi/86400$ or $72.7\times10^{-6}$ radians (i.e., $\sec^{-1}$). t is the time of day measured in seconds. $\delta$ is the phase delay in radians. A is the magnitude of the circadian compensation factor, usually represented in decibels. In a preferred form of the invention, the circadian compensation factor has a value of 0.5 dB, although values from 0.5 to 2 dB are common. If both p(t) and $\Delta(t)$ are expressed in decibels, then the modified time-varying electrical parameter $p_m(t)$ is given by Equation 2, $$p_m(t)=p(t)+\Delta(t) \quad \text{Eq. 2}$$

With A=0.5 dB, the CCF modulates the stimulation intensity by a multiplicative factor ranging from 0.94 to 1.06 (i.e., approximately ±6%). For example, if the purpose of the CCF is to regulate pulse charge with a baseline value of 10 µC, then the CCF will modulate the pulse charge from 9.4 µC to 10.6 µC depending on the time of day. $\delta$ is the phase delay of the circadian rhythm, measured in radians. FIG. 6 shows an example of a CCF 640 that offsets a circadian rhythm of the electrotactile perception threshold 610. In this example, the electroctactile perception threshold of the circadian rhythm has a minimum threshold 617 at time 642 (8 PM or Hour 20) and therefore the CCF 640 also has its minimum 641 at time 642 (8 PM or Hour 20). The phase delay $\delta$ 643 is $2\pi/2/24$). There is no net effect on pulse charge over the course of a day.

An important assumption implicit in the CCF of Equation 1 is that the circadian rhythm follows a sinusoidal pattern. Circadian rhythms typically exhibit features of sinusoidal rhythms, repeatedly ascending to a maximum value, steadily decreasing to a minimum value and then increasing again. Therefore, mathematical models of circadian rhythms often utilize sine and cosine functions. This approach appears to provide a good fit to many types of circadian data such as core body temperature. In some instances, non-sinusoidal shapes such as square wave or triangle wave approximations better match the data. Although the preferred embodiment utilizes a sinusoidal function, alternative circadian rhythm models may be used and fall within the scope of the invention.

The CCF must be customized for each user. The most straightforward approach for customizing the CCF for each user is to ask the user what time of the day the uncompensated TENS stimulation feels strongest in the case of constructing a circadian rhythm of the electrotactial perception threshold. Similarly, a circadian rhythm for the pain intensity is constructed by identifying the time when is the pain level is the greatest. In one preferred embodiment, the CCF is then "shifted" in time to match the specified timing information provided by the user. Another approach to customize the CCF for individuals is to measure relevant physiological parameters such as skin temperature, skin impedance, and Galvanic skin response over the course of a day. Measurements from several days can also be used to calculate an average CCF (i.e., by using a processor included in TENS device 100 for creating a circadian compensation profile and determining compensation values, as will hereinafter be discussed in further detail). In another form of the invention, measured physiological values as a function of measurement time are used by the processor 515 to calculate the CCF. In yet another form of the invention, a suitable function with parametric model parameters is fitted to the measured values to calculate the CCF. And in another form of the invention, an initial CCF profile can be created based on demographic and physiological characteristics of the user, which may be used to calculate the CCF for a particular user. Subsequently manual adjustments of TENS stimulation parameters by the user can be used to refine the initial (i.e., calculated) CCF.

Figure 7:
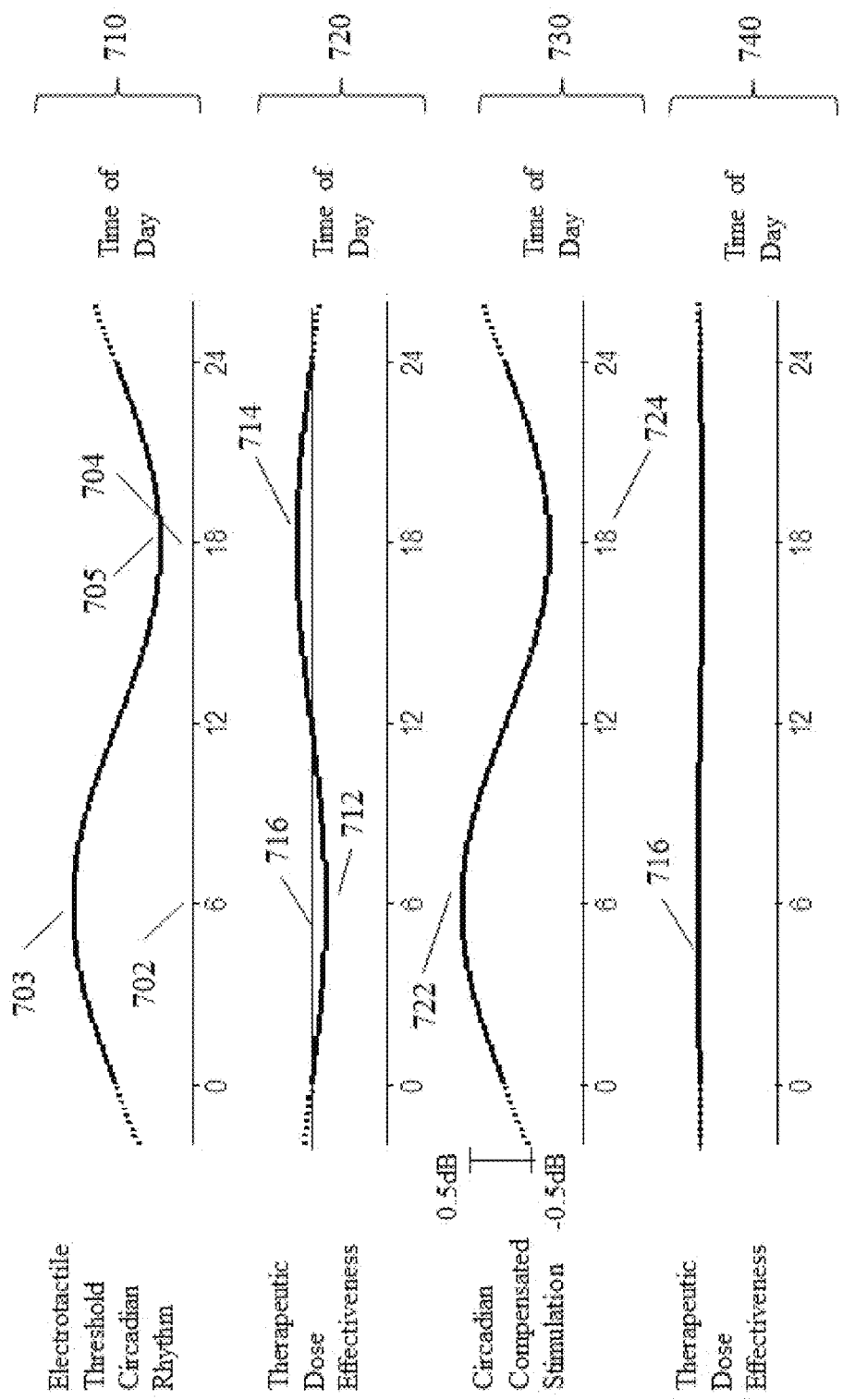
FIG. 7 is schematic view showing an example of the use of a circadian compensation function to compensate for the impact of circadian rhythm on the electrotactile perception threshold.

FIG. 7 shows how the CCF corrects for the impact of a circadian rhythm on the electrotactile perception threshold for an exemplary user. The top graph 710 shows a 24-hour circadian rhythm of the electrotactile perception threshold. In this example, the electrotactile perception threshold is at maximum at 6:00 AM (702) and a minimum at 6:00 PM (704). The second graph 720 shows the impact of circadian variation in the electrotactile perception threshold on the effective stimulation intensity for a constant stimulation intensity. The horizontal line 716 represents the target stimulation level, which in the absence of temporal variation in the electrotactile perception threshold would result from constant stimulation intensity. Values above the horizontal 716 indicate an effective stimulation intensity above the target stimulation level and values below the horizontal 716 indicate an effective stimulation intensity below the target stimulation level. When the electrotactile perception threshold 710 is at its maximum 703 (i.e., at 6:00 AM, indicated at 702 in FIG. 7), the effective stimulation intensity is at a minimum 712 because fewer nerve fibers are stimulated or their integrated signal in the CNS is attenuated (i.e., due to modulation of the stimulation intensity to take into account the effects of circadian rhythm). Conversely when the electrotactile threshold is at its minimum 705 (i.e., at 6:00 PM, indicated at 704 in FIG. 7), the effective stimulation intensity is at its maximum 714. This is because more nerve fibers are stimulated or their integrated signal in the CNS is amplified (i.e., due to modulation of the stimulation intensity to take into account the effects of circadian rhythm). The third graph 730 shows the CCF derived from Equation 1 for this particular circadian rhythm 710. The CCF function has maximum 722 and minimum 724 times (i.e., 6:00 AM and 6:00 PM, respectively) which match the underlying circadian rhythm 710. In this example, we assume A=0.5 dB so the CCF scales from a maximum 722 of 0.5 dB to a minimum 724 of −0.5 dB. The bottom graph 740 shows the effective stimulation intensity after modulation by the CCF 730 (i.e., after fluctuations in stimulation modulation resulting from circadian rhythm have been corrected for by applying CCF 730 to a default constant stimulation intensity). The effective stimulation intensity 740 now approximates the target stimulation level 716 throughout the entire 24-hour period.

The circadian compensation function (CCF) represented in Equation 1 can be expanded to account for more than one simultaneous sinusoidal circadian rhythm, with each of the multiple simultaneous sinusoidal circadian rhythms being approximated by a sinusoid as represented in Equation 3, $$\Delta(t) = \Sigma_{i=1}^{N} A_i \sin(\omega t + \delta_i) \quad \text{Eq. 3}$$

Where $A_i$ is the amplitude and $\delta_i$ is the phase of the $i^{th}$ circadian rhythm. This generalized model makes a number of assumptions. Most notably, this generalized model assumes that the impact of multiple circadian rhythms on TENS are independent. As a result, the individual circadian compensation functions can be summed to create a composite circadian compensation function that will compensate for the integrated effect of the individual circadian rhythms. This is a reasonable first order approximation. The more generalized model can be written as shown in Equation 4, $$\Delta(t) = A \sin(\omega t + \phi) \quad \text{Eq. 4}$$

where A and $\phi$ are functions of both $\{A_1 \ldots A_N\}$ and $\{\delta_1 \ldots \delta_N\}$. In one form of the invention, the individual circadian rhythms may not have an independent effect on TENS. In other words, there may be cross-interactions between the individual circadian rhythms.

Figure 8:
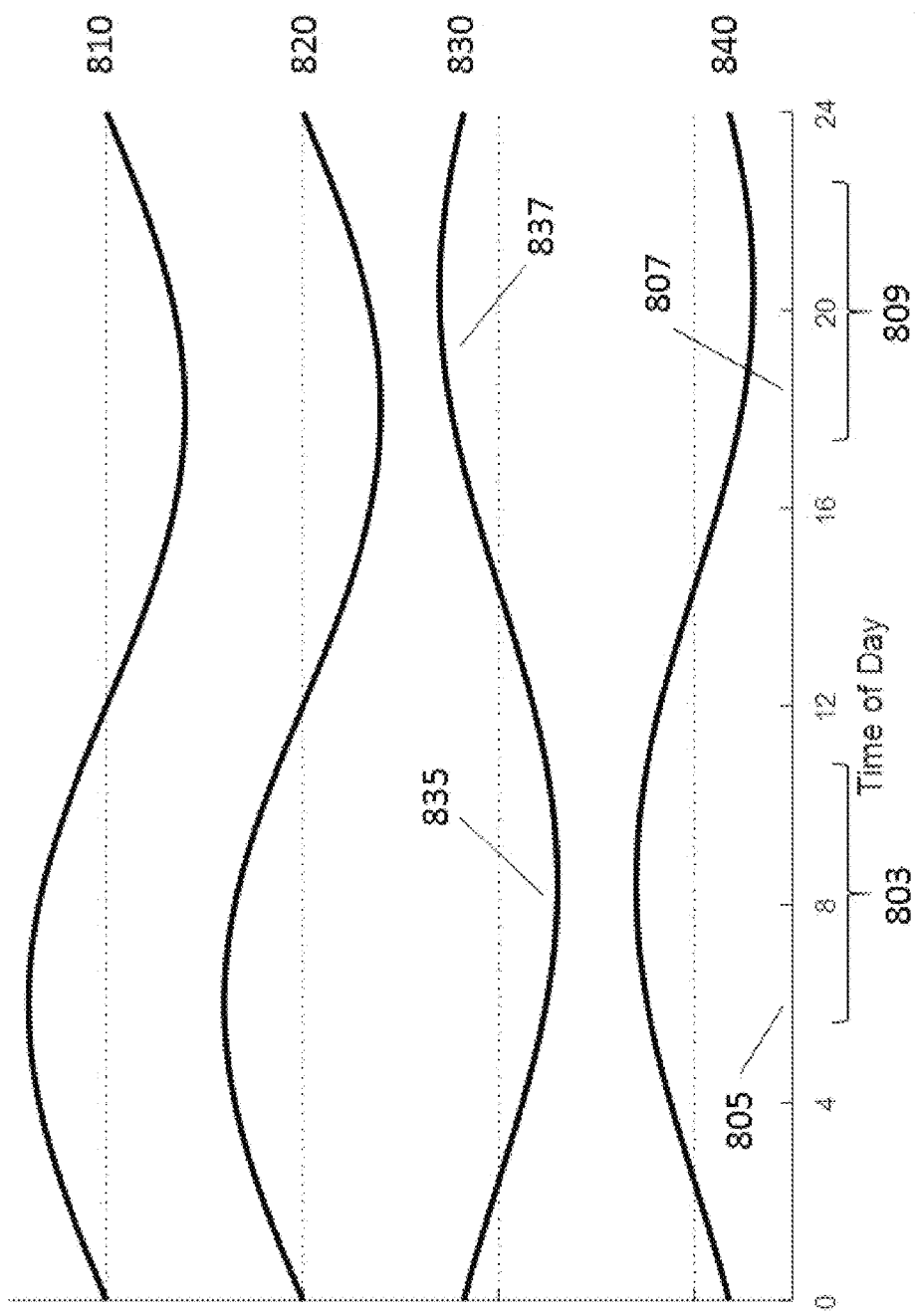
FIG. 8 is a schematic view showing exemplary adjustments to more than one stimulation parameter in order to compensate for the effect of circadian rhythm on the electrotactile perception threshold and pain intensity.

In one preferred form of the invention, circadian compensation of multiple circadian rhythms is accomplished through modulation of one stimulation parameter, such as stimulation pulse intensity. In another preferred form of the invention, circadian compensation is achieved through modulation of multiple stimulation parameters (e.g., stimulation pulse intensity and time delay between stimulation sessions). An example is illustrated via FIG. 8. As shown in FIG. 8, an exemplary user's electrotactile perception threshold circadian rhythm 810 is determined through objective physiological measurement (e.g., Galvanic skin response or skin impedance from a Galvanic response detector, as will hereinafter be discussed in further detail). Accordingly, stimulation intensity 820 is modulated to peak around 805 (i.e., Hour 6 or 6:00 AM) and to bottom around 807 (i.e., Hour 18 or 6:00 PM) whereby to maintain the "strong yet comfortable" TENS stimulation sensation. The pain intensity pattern 830, determined from subjective feedback from the user, is most intense 837 in the evening time period 809 and least intense 835 in the morning time period 803. In order to provide appropriate TENS therapy doses that match the pain intensity pattern 830 under the condition that the electrotactile perception threshold 810 is out of phase with the pain intensity pattern 830, a second stimulation parameter is modulated. By way of example but not limitation, the second stimulation parameter is the time period between two consecutive therapy sessions (i.e., the stimulation session gap) 840; a shorter period is used in the evening time 809 and a longer period is used in the morning 803.

Exemplary Operation

In one preferred form of the invention, TENS device 100 comprises a circadian rhythm processor 515 and a controller 520. TENS device 100 is configured/programmed to operate in the manner shown in FIG. 4.

More particularly, when TENS device 100 is secured to the upper calf 140 of the user and turned on, processor 515 collects data from accelerometer 172, real-time clock 505, temperature sensor 107, ambient light detector 510, and skin impedance and Galvanic response detector 109. Time from real-time clock 505 is used to determine the compensation values. User state (e.g., active, asleep, rest) based on accelerometer 172 and/or other sensors (e.g., light detector 510, temperature sensor 107, etc.) can also be used to determine the compensation values at a given time.

A compensation profile is created by processor 515 using a pre-loaded compensation profile which is universal to all TENS users (i.e., a pre-loaded compensation profile which is already stored in TENS device 100, i.e., in appropriate hardware and software of the sort well known in the art). The pre-loaded compensation profile can also be based on disease state transmitted from a user input module 512 or pain intensity profile transmitted from user input module 512. It should be appreciated that user input module 512 may comprise a data connection (e.g., a USB cable) tethered to an external computer, a wireless connection to a smartphone 860 configured with appropriate software for permitting user input and wirelessly communicating with TENS device 100, etc.). The compensation profile can be based on (or updated in response to) physiological measurements from skin temperature sensor 107, or the skin impedance and a Galvanic response detector 109 (FIG. 4). The compensation profile can be updated by the processor 515 based on input from user input module 512 indicating perceived stimulation intensity (too strong, not strong enough) or indicating the pain intensity at various time instances. The compensation profile is used by processor 515 to calculate a compensation value (e.g., a circadian compensation function).

The compensation value calculated by the processor 515 is transmitted to the controller 520. The controller 520 in turn modifies one or more stimulation parameters such as stimulation pulse intensity, pulse width, pulse frequency, therapy session duration, or the time delay between sessions in order to deliver the optimal and stable pain control.

Data from skin impedance and Galvanic response detector 109, temperature sensor 107, or accelerometer 172 can be used to determine the pain-relieving effect of the TENS stimulation. By way of example but not limitation, more restful sleep at night can be quantified by the accelerometer data (i.e., since more restful sleep results in less movement of the user's body). If sleep measurements improve with the introduction of a modification to the circadian compensation profile, then the processor 515 can incorporate that information to strengthen the modification. If the sleep quality degenerates with a change to the compensation profile, processor 515 may discount the change to the compensation profile.

Figure 9:
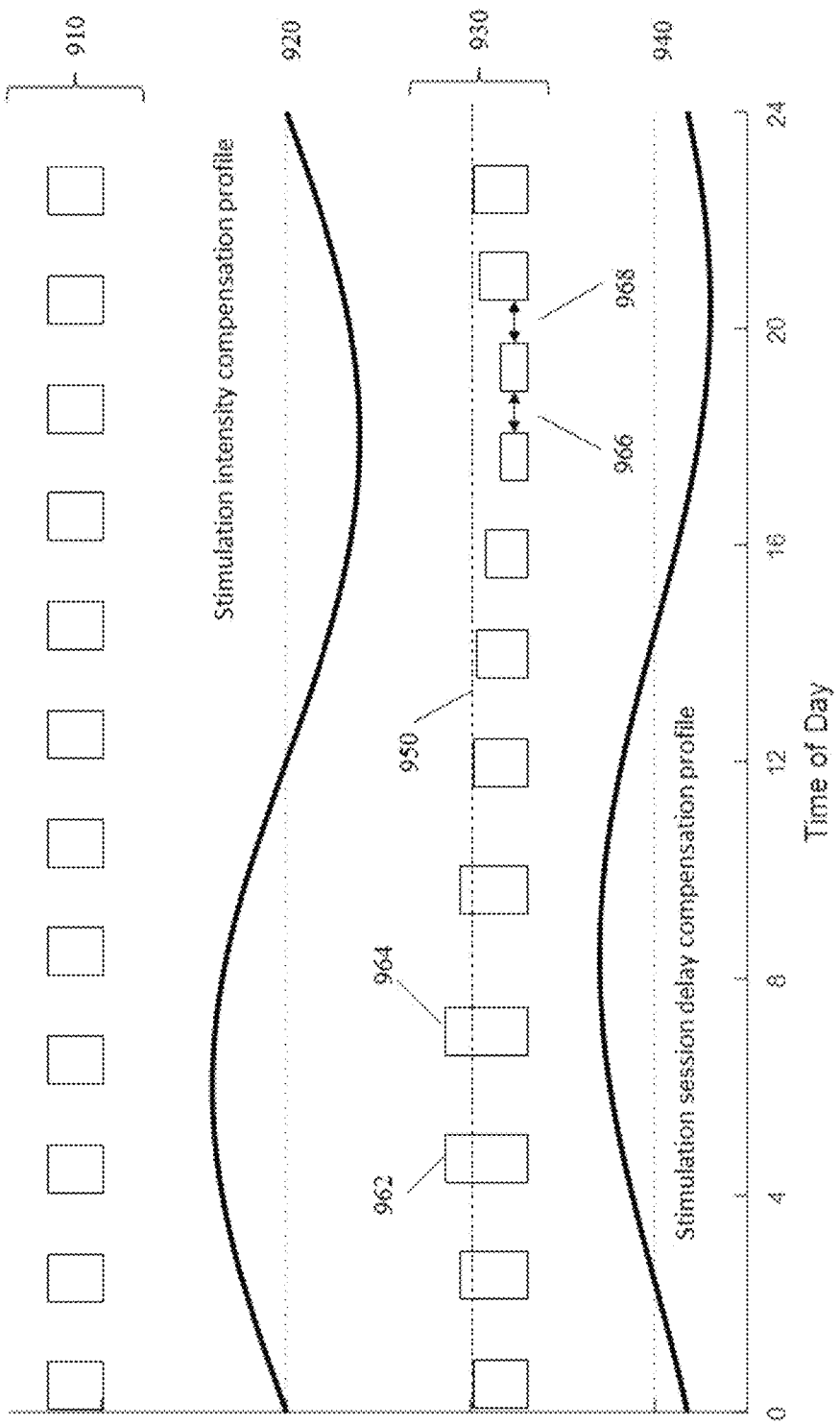
FIG. 9 is a schematic view showing an example of TENS therapy session stimulation patterns after circadian compensations have been applied to the stimulation intensity and the time delay between TENS therapy sessions.

FIG. 9 illustrates the impact of the compensation profiles on TENS therapy session behavior on a 24-hour scale. Boxes 910 represent 12 therapy sessions each of one-hour duration with a fixed stimulation intensity and one-hour delay between consecutive sessions. The height of each box corresponds to the stimulation intensity (however, it should be appreciated that boxes 910 are not necessarily drawn to scale). Stimulation intensity compensation profile 920, which is the same as the aforementioned stimulation intensity profile 820 shown in FIG. 8, peaks (i.e., reaches its maximum value) in the morning due to higher electrotactile perception threshold 810. The stimulation intensity compensation profile 920 reaches its minimum value in the evening. The therapy session delay compensation profile 940, which is the same as the aforementioned stimulation session gap 840 shown in FIG. 8, is shortest in the evening and longest in the morning to match the pain-relieving dose requirement corresponding to a pain intensity profile 830. Boxes 930 represent therapy sessions modulated by the two compensation profiles 920 and 940. The compensation profile 920 causes the stimulation intensity to increase from its default value (indicated by dash line 950), as evidenced by sessions 962 and 964, in order to match higher electrotactile perception threshold in the early morning period. Similarly, the stimulation intensity is smaller than the default level in the evening. The compensation profile 940, on the other hand, causes the period between therapy sessions to change from the default one-hour value. The periods 966 and 968 are shorter than one-hour, leading to more frequent therapy sessions in order to match the requirements of a higher pain intensity experienced by the user in the evening.

Modifications Of The Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. Apparatus for transcutaneous electrical nerve stimulation in a user, the apparatus comprising:
   stimulation means for electrically stimulating at least one nerve with at least one stimulation pulse, wherein the stimulation pulse is delivered to the skin of the patient;
   control means connected to said stimulation means for controlling at least one characteristic of said at least one stimulation pulse; and
   modulating means connected to the control means for automatically modulating said at least one characteristic of said at least one stimulation pulse according to at least one circadian rhythm;
   wherein said at least one characteristic comprises at least one from the group consisting of pulse amplitude, pulse width, pulse charge and pulse frequency.

2. Apparatus according to claim 1 wherein said at least one characteristic is the duration of the therapy session.

3. Apparatus according to claim 1 wherein said at least one characteristic is the time between two consecutive therapy sessions.

4. Apparatus according to claim 1 wherein said modulating means comprises a periodic function.

5. Apparatus according to claim 4 wherein said periodic function is a sinusoid with a 24-hour period.

6. Apparatus according to claim 4 wherein said periodic function is a biphasic square wave with a 24-hour period.

7. Apparatus according to claim 4 wherein said periodic function is a biphasic triangular wave with a 24-hour period.

8. Apparatus according to claim 1 wherein said modulation comprises a multiplication operation.

9. Apparatus according to claim 8 wherein said multiplication is by values ranging from 0.94 to 1.06.

10. Apparatus according to claim 1 wherein said modulation means is initialized according to health conditions of the user.

11. Apparatus according to claim 1 wherein feedback from the user alters said modulation means.

12. Apparatus according to claim 11 wherein said feedback is an indication of pain intensity by the user.

13. Apparatus according to claim 11 wherein said feedback is physiological measurement from the user.

14. Apparatus according to claim 13 wherein said physiological measurement is the user's electrotactile perception threshold.

15. A method for controlling transcutaneous electrical nerve stimulation based on the time of day, the method comprising the steps of:
   providing apparatus for transcutaneous electrical nerve stimulation in a user, the apparatus comprising:
      stimulation means for electrically stimulating at least one nerve with at least one stimulation pulse, wherein the stimulation pulse is delivered to the skin of the patient;
      control means connected to said stimulation means for controlling at least one characteristic of said at least one stimulation pulse; and
      modulating means connected to the control means for modulating said at least one characteristic of said at least one stimulation pulse;
      wherein said at least one characteristic comprises at least one from the group consisting of pulse amplitude, pulse width, pulse charge and pulse frequency;
   determining a time-varying function within a 24-hour period;
   using said stimulation means to electrically stimulate at least one nerve; and
   modulating at least one characteristic of said electrical stimulation according to the time of day and said time-varying function.

16. A method according to claim 15 wherein said time-varying function is a sinusoid.

17. A method according to claim 15 wherein said time-varying function is a biphasic square wave.

18. A method according to claim 15 wherein said modulation consists of application of a multiplicative factor from said time-varying function to said at least one characteristic of said at least one electrical stimulation pulse.

19. Apparatus for transcutaneous electrical nerve stimulation in a user, the apparatus comprising:
   stimulation means for electrically stimulating at least one nerve with at least one stimulation pulse, wherein the stimulation pulse is delivered to the skin of the patient;
   control means connected to said stimulation means for controlling at least one characteristic of said at least one stimulation pulse; and
   modulating means connected to the control means for automatically modulating said at least one characteristic of said at least one stimulation pulse according to at least one circadian rhythm;
   wherein said at least one characteristic comprises at least one from the group consisting of pulse amplitude, pulse width, pulse charge and pulse frequency;
   and further wherein the ratio between the duration of a therapy session and the time between two consecutive therapy sessions remains constant.

* * * * *